(12) United States Patent
Stern (10) Patent No.: US 8,808,170 B2
(45) Date of Patent: Aug. 19, 2014

(54) MULTIPLE-CHANNEL ENDOSCOPIC BIOPSY SHEATH

(76) Inventor: Mark A. Stern, Atlanta, GA (US)

( * ) Notice: Subject to any disclaimer, the term of this patent is extended or adjusted under 35 U.S.C. 154(b) by 457 days.

(21) Appl. No.: 13/038,148

(22) Filed: Mar. 1, 2011

(65) Prior Publication Data

US 2011/0224492 A1 Sep. 15, 2011

Related U.S. Application Data

(60) Provisional application No. 61/312,407, filed on Mar. 10, 2010.

(51) Int. Cl.
| | |
|---|---|
| *A61B 1/00* | (2006.01) |
| *A61B 1/018* | (2006.01) |
| *A61B 10/04* | (2006.01) |
| *A61B 17/24* | (2006.01) |
| *A61B 17/00* | (2006.01) |
| *A61B 17/29* | (2006.01) |
| *A61B 17/34* | (2006.01) |
| *A61B 17/3205* | (2006.01) |
| *A61B 10/06* | (2006.01) |

(52) U.S. Cl.
CPC ............ *A61B 17/3421* (2013.01); *A61B 17/24* (2013.01); *A61B 1/018* (2013.01); *A61B 10/04* (2013.01); *A61B 2017/0034* (2013.01); *A61B 17/29* (2013.01); *A61B 2017/3447* (2013.01); *A61B 1/0014* (2013.01); *A61B 2017/00269* (2013.01); *A61B 1/00135* (2013.01); *A61B 17/32056* (2013.01); *A61B 10/06* (2013.01)
USPC .......................................... 600/153; 600/104

(58) Field of Classification Search
CPC ...... A61B 1/012; A61B 1/0125; A61B 1/018; A61B 10/04; A61B 17/3421; A61B 1/00135; A61B 1/0014; A61B 10/06; A61B 2017/3447; A61B 17/29; A61B 17/32056; A61B 2017/00269; A61B 2017/0034; A61B 17/24
USPC .......................... 600/153, 121–123, 104, 113
See application file for complete search history.

(56) References Cited

U.S. PATENT DOCUMENTS

| | | | | |
|---|---|---|---|---|
| 4,616,631 | A  * | 10/1986 | Takahashi ...................... | 600/139 |
| 5,349,941 | A  * | 9/1994 | Hori .............................. | 600/122 |
| 5,944,654 | A  * | 8/1999 | Crawford ....................... | 600/157 |
| 6,352,503 | B1 * | 3/2002 | Matsui et al. .................. | 600/104 |
| 6,585,642 | B2 * | 7/2003 | Christopher ................... | 600/156 |
| 6,878,106 | B1 * | 4/2005 | Herrmann ...................... | 600/104 |
| 7,150,713 | B2 * | 12/2006 | Shener et al. .................. | 600/156 |
| 7,762,949 | B2 * | 7/2010 | Nakao ............................ | 600/153 |
| 8,016,749 | B2 * | 9/2011 | Clerc et al. .................... | 600/117 |
| 2005/0085695 | A1* | 4/2005 | Shener et al. .................. | 600/156 |
| 2005/0148816 | A1* | 7/2005 | Glukhovsky et al. .......... | 600/103 |
| 2006/0206118 | A1* | 9/2006 | Kim et al. ....................... | 606/86 |
| 2007/0252892 | A1* | 11/2007 | Fujita et al. .................... | 348/65 |

(Continued)

*Primary Examiner* — John P Leubecker
*Assistant Examiner* — Arnaldo Torres Diaz
(74) *Attorney, Agent, or Firm* — Sutherland Asbill & Brennan LLP (57) ABSTRACT

Embodiments of the invention provide devices and associated methods for use when performing endoscopic procedures. According to one aspect, a sheath positionable within a working channel of an endoscopic device, and adapted for receiving one or more instruments, is provided. The sheath can include a first channel and a second channel, the first channel and the second channel extending at least partially along a length of the sheath, wherein at least one of the first channel or the second channel includes an open edge open along at least part of the length of the respective channel.

12 Claims, 7 Drawing Sheets

(56) References Cited

U.S. PATENT DOCUMENTS

| | | | |
|---|---|---|---|
| 2008/0033257 A1* | 2/2008 | Yokoi et al. | 600/300 |
| 2008/0154124 A1* | 6/2008 | Iustin et al. | 600/424 |
| 2008/0297291 A1* | 12/2008 | Kawano et al. | 335/285 |
| 2009/0043164 A1* | 2/2009 | Hasegawa et al. | 600/118 |
| 2009/0093678 A1* | 4/2009 | Kimura et al. | 600/117 |
| 2010/0179782 A1* | 7/2010 | Kimura et al. | 702/94 |
| 2010/0204566 A1* | 8/2010 | Uchiyama et al. | 600/424 |
| 2010/0305426 A1* | 12/2010 | Kimura et al. | 600/411 |
| 2011/0181273 A1* | 7/2011 | Iida et al. | 324/207.11 |
| 2011/0184690 A1* | 7/2011 | Iida et al. | 702/150 |
| 2011/0208019 A1* | 8/2011 | Sato et al. | 600/302 |
| 2011/0224490 A1* | 9/2011 | Kimura et al. | 600/118 |
| 2011/0255757 A1* | 10/2011 | Nishimura et al. | 382/128 |
| 2011/0255758 A1* | 10/2011 | Nishimura et al. | 382/128 |
| 2011/0255759 A1* | 10/2011 | Nishimura et al. | 382/128 |
| 2011/0273548 A1* | 11/2011 | Uchiyama et al. | 348/68 |
| 2012/0143047 A1* | 6/2012 | Kimura et al. | 600/424 |

* cited by examiner

MULTIPLE-CHANNEL ENDOSCOPIC BIOPSY SHEATH

CROSS REFERENCE TO RELATED APPLICATIONS

This application claims priority to U.S. Provisional Patent Application Ser. No. 61/312,407 filed Mar. 10, 2010, which is incorporated by reference in its entirety.

FIELD OF THE INVENTION

The invention relates generally to devices for use during endoscopic surgical procedures, and methods pertaining thereto, and more particularly to a multiple-channel endoscopic biopsy sheath.

BACKGROUND OF THE INVENTION

Polyps represent growth of tissue that occurs in any area within a mucous membrane. More particularly, polyps are often found within the gastrointestinal tract, specifically the colon and less so in the esophagus, small bowel and stomach. Although most polyps are benign, a minority can develop into cancer. It is the practice to screen adults to remove polyps of the colon when encountered by performing a polypectomy procedure. The malignant potential of a polyp is based upon multiple characteristics including size, histopathology and contour defined as pedunculated (on a stalk), sessile, (domed growth), and the more recently evaluated flat polyp which is thought to have a greater malignant potential.

It is therefore of utmost importance to be able to completely remove these polyps when encountered. Due to the physical nature of a flat polyp, in particular, it can be technically more of a challenge to remove completely and safely. A design to grasp and remove these polyps in the safest manner is of paramount importance in the field of endoscopy.

Generally, there are 3 basic designs for instruments to remove polyps, in addition to a few specially designed instruments that are used more rarely. The 3 basic designs include cold biopsy/grasping jaws, hot biopsy grasping jaws (with cautery), and a snare (with cautery). These three designs account for greater than 95% of the instruments used during polypectomy procedures. During a typical procedure one, two or all three of these instruments may be used.

There, however, remains a need in the art for improved biopsy instruments for use during endoscopic procedures.

SUMMARY OF THE INVENTION

Various embodiments described herein provide devices and associated methods for use when performing endoscopic procedures. According to one aspect, a sheath positionable within a working channel of an endoscopic device, and adapted for receiving one or more instruments, is provided. The sheath can include a first channel and a second channel, the first channel and the second channel extending at least partially along a length of the sheath, wherein at least one of the first channel or the second channel includes an open edge open along at least part of the length of the respective channel.

In one embodiment, the cross-section of the sheath defines an approximately hyperbolic shape. The hyperbolic shape permits gas or fluid flow between an outer surface of the sheath and an inner surface of the endoscopic device.

In one embodiment, the first channel has a first length and the second channel has a second length, wherein the second length is less than the first length. In one embodiment, the distal end of the first channel and the distal end of the second channel are spaced apart along the length of the sheath. In one embodiment, the proximal end of the first channel and the proximal end of the second channel are spaced apart along the length of the shaft.

In one embodiment, an instrument is insertable into and removable from the second channel through the open edge.

In one embodiment, a snare instrument is insertable into the first channel. The snare instrument may include a snare end having a preformed shape, such as a shape memory material, wherein the preformed shape causes the snare instrument to intersect the longitudinal axis of the second channel when extended from the distal end of the first channel.

According to another aspect of this invention, an apparatus positionable within a working channel of a device is provided. The apparatus may include a sheath having a plurality of channels extending at least partially along a length of the sheath, wherein at least one of the plurality of channels includes an open edge open along at least part of the length of the respective channel.

According to one embodiment of this aspect, a second one of the plurality of channels is enclosed along the length of the respective channel.

According to yet another aspect, a biopsy device is provided. The biopsy device may include a sheath having a first channel and a second channel, wherein at least one of the first channel and the second channel has an open edge open along at least part of the length of the respective channel. The biopsy device may also include a snare instrument adapted for insertion into one of the first channel or the second channel and a forceps instrument adapted for insertion into the other one of the first channel or the second channel.

According to yet another aspect, a biopsy kit is provided. The biopsy kit may include a sheath comprising a first channel and a second channel, wherein at least one of the first channel or the second channel has an open edge open along at least part of the length of the respective channel.

In one embodiment, the kit may further include a snare instrument adapted for insertion into one of the first channel or the second channel, a forceps instrument adapted for insertion into one of the first channel or the second channel, and/or an endoscopic device with a working channel extending therethrough, wherein the sheath is adapted for insertion through the working channel.

In one embodiment, the kit may further include a cauterization mechanism operably connectable to an instrument insertable through at least one of the first channel or the second channel.

According to yet another aspect of the invention, a method of performing a biopsy procedure is provided. The method may include: deploying an endoscopic device having a working channel extending therethrough to a procedure site; providing a sheath, wherein the sheath includes a first channel and a second channel, and wherein at least one of the first channel or the second channel has an open edge open along at least part of the length of the respective channel; inserting a first instrument through the first channel of the sheath; inserting a second instrument through the second channel of the sheath; inserting the sheath through the proximal end of the working channel of the endoscopic device; and performing the biopsy procedure using the first instrument and the second instrument.

According to one embodiment, the method may include extending the forceps instrument through a snare end of the snare instrument; grasping tissue with the forceps instrument; extracting the tissue through the snare end of the snare instrument with the forceps instrument, causing the snare end to encircle the tissue; tightening the snare around the tissue, causing removal of the tissue; and extracting the tissue with the forceps instrument.

According to one embodiment, the method may include manipulating the second instrument by grabbing a shaft of the second instrument at a point between the proximal end of the first channel and the proximal end of the second channel.

According to yet another embodiment, the method may include removing the second instrument from the channel having the open edge through the open edge. The second instrument may be used for another procedure after removal from the sheath. In addition, a third instrument may be inserted within the channel through the open edge.

According to one embodiment, the biopsy procedure performed by the method may include removing a flat polyp. In another embodiment, the method may include removing a pedunculated polyp.

According to yet another aspect, a method for manufacturing a sheath is provided, wherein the sheath comprises a first channel and a second channel, and wherein at least one of the first channel or the second channel comprises an open edge open along at least part of the length of the respective channel.

According to yet another aspect, a sheath positionable within a working channel of an endoscopic device and for receiving one or more instruments is provided. The sheath includes a first channel and a second channel, the first channel and the second channel extending at least partially along a length of the sheath, wherein the second channel is shorter than the first channel.

According to one embodiment, the proximal end of the first channel extends proximally beyond the proximal end of the second channel. According to one embodiment, the distal end of the first channel extends distally beyond the distal end of the second channel.

BRIEF DESCRIPTION OF THE DRAWINGS

The objects and advantages of the present invention will be better understood and more readily apparent when considered in conjunction with the following detailed description and accompanying drawings which illustrate, by way of example, embodiments of multiple-channel biopsy sheath devices, and in which.

DETAILED DESCRIPTION OF THE PREFERRED EMBODIMENTS

As required, detailed embodiments of the invention are disclosed herein. However, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the invention in virtually any appropriately detailed structure.

Embodiments of the invention provide multiple-channel endoscopic biopsy sheath devices and corresponding methods for their use and manufacture. The multiple-channel endoscopic biopsy sheath devices and methods described herein are used to facilitate polypectomy procedures conducted through a working channel of an endoscopic device in a safer, more effective, and more cost-effective manner. Specifically, example multiple-channel endoscopic biopsy sheath devices may include a sheath that has at least two channels (e.g., a first channel and a second channel) formed therethrough. The two (or more) channels are for receiving and guiding two instruments therethrough, such as a forceps instrument and a snare instrument, both of which, when used together, facilitating more effective polypectomy procedures. In addition, a sheath having separate channels allows for independent advancement and retraction of the instruments through the channels to permit better coordination and use of the two instruments together. According to one embodiment of the invention, the two channels of the sheath are integral with the sheath, such that they embody a single apparatus. Moreover, in one embodiment, the cross-section of the sheath has sides with an approximately hyperbolic shape (e.g., similar to a figure eight), which advantageously minimizes the overall diameter of the sheath and permits gas and/or fluid flow between the sheath and the wall of the working channel of the endoscope. In addition, according to one embodiment, at least one of the channels has an open edge defined along the length of the channel (or at least partially along the length of the channel). This open edge reduces the overall diameter of the sheath, permits additional movement of an instrument contained therein, and allows for easy removal and exchange of instruments through the open edge.

It is appreciated that the above-described multiple-channel endoscopic biopsy sheath devices are exemplary only, and that additional and/or different features can be included, as further described in more detail herein. For example, the length and orientation of the two channels relative to each other may vary according to some embodiments.

Embodiments of multiple-channel endoscopic biopsy sheath devices and corresponding methods are further described with reference to FIGS. 1-7.

Figure 1A:
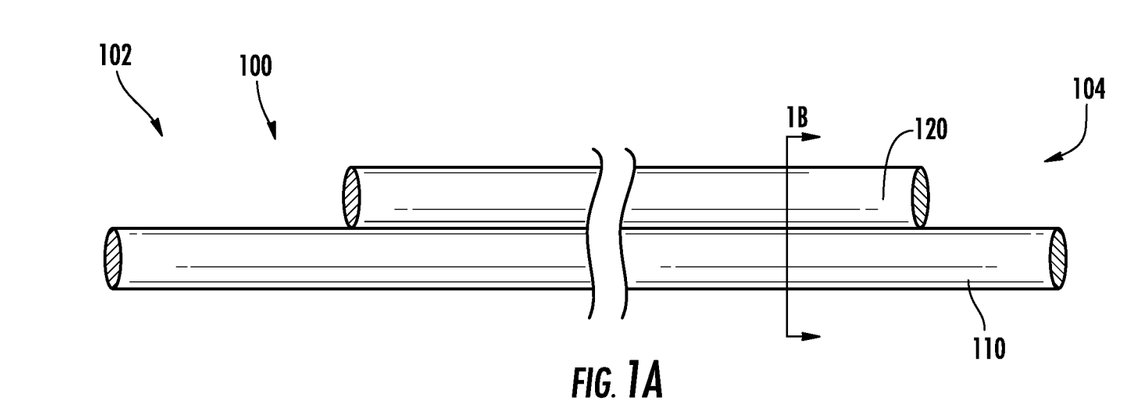
FIG. 1A is a profile view schematic diagram of a biopsy sheath, according to an example embodiment.

With reference to FIG. 1A, a profile view schematic diagram of a biopsy sheath is shown, according to an example embodiment. The biopsy sheath 100 of this embodiment includes a first channel 110 and a second channel 120. The first channel 110 and the second channel 120 are integrated and together form the biopsy sheath 100.

Figure 1B:
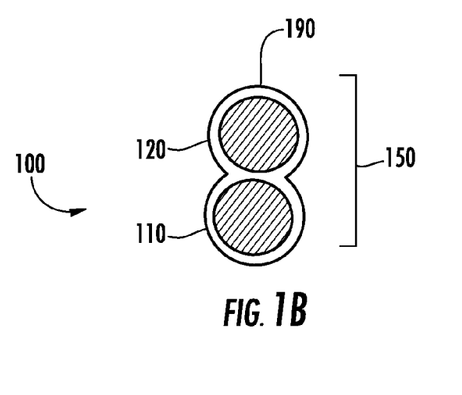
FIG. 1B is a cross-sectional view schematic diagram of a biopsy sheath, according to an example embodiment.
Figure 2A:
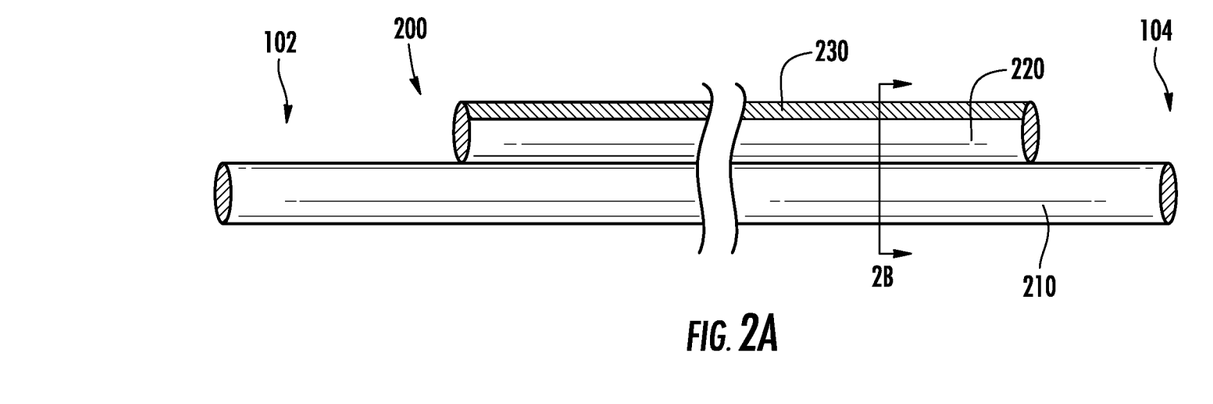
FIG. 2A is a profile view schematic diagram of a biopsy sheath, according to an example embodiment.
Figure 2B:
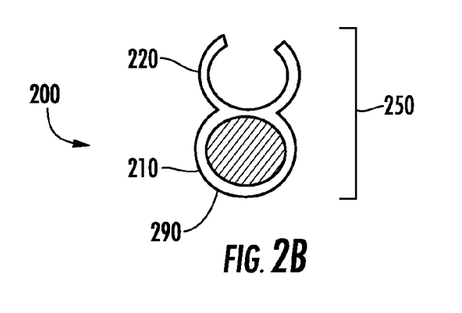
FIG. 2B is a cross-sectional view schematic diagram of a biopsy sheath, according to an example embodiment.

FIG. 2A shows a profile view schematic diagram of a biopsy sheath 200 is shown, according to another example embodiment, in which the biopsy sheath 200 includes a first channel 210 and a second channel 220 like that illustrated in FIG. 1. However, according to this embodiment, the second channel 220 is open along the length of the channel from its distal end to its proximal end, which defines an open edge 230. FIGS. 1B and 2B illustrate the approximately hyperbolic cross section 190, 290 of each embodiment biopsy sheath 100, 200, respectively. These two cross-sectional views illustrate the differences between the enclosed channel configuration of the second channel 120 in FIG. 1B and the open edge 230 of the second channel 220 in FIG. 2B.

Figure 2C:
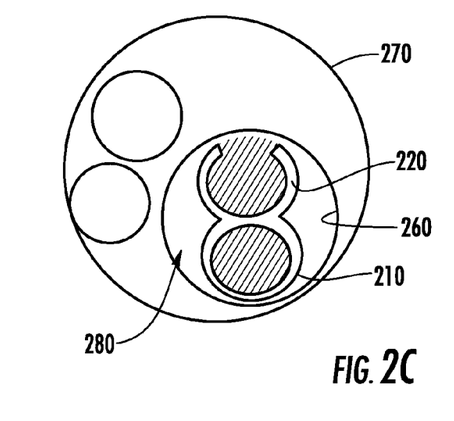
FIG. 2C is a cross-sectional view schematic diagram of an endoscopic device and a biopsy sheath, according to an example embodiment.

In embodiments having at least one channel with an open edge, such as the open edge 230 shown in FIGS. 2A-2C, the biopsy sheath 200 may have a smaller overall diameter 250, as compared to the overall diameter 150 of the biopsy sheath 100, while still providing the same or similar internal diameters of each channel and accommodating the same or similar sizes of instruments therein. A smaller overall diameter 250 of a biopsy sheath is beneficial because the working channel of a conventional endoscopic device is typically limited in size, and thus difficult to accommodate multiple instruments therethrough. FIG. 2C, which is a cross-sectional view schematic diagram of an endoscopic device 270, shows that, by creating an open edge 230 in the second channel 220 of the biopsy sheath 200, the overall diameter 250 can be reduced, while still allowing an instrument to be retained therein because the walls of the second channel 220 abut the inner wall 260 of an endoscopic device's 270 working channel 280, effectively enclosing the second channel 220. In other embodiments, instead of reducing the overall diameter of the biopsy sheath 200, the open edge 230 permits increasing the inner diameters of one or both of the first channel 210 and the second channel 220 while retaining the same, similar, or slightly smaller diameter as the inner diameter of a working channel of an endoscopic device 270. Accordingly, in some embodiments, due to the open edge 230, larger inner diameters of the biopsy sheath 200 can accommodate larger instruments than would otherwise fit within a dual-channel biopsy sheath intended for use with the same size working channel.

Figure 1C:
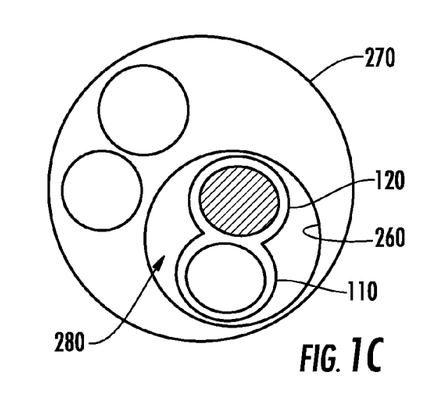
FIG. 1C is a cross-sectional view schematic diagram of an endoscopic device and a biopsy sheath, according to an example embodiment.

FIG. 1C illustrates a cross-sectional view schematic diagram of an endoscopic device 270 having the same size working channel 280 and a biopsy sheath having two entirely enclosed channels, such as the channels 110, 120 of the biopsy sheath 100 illustrated in FIGS. 1A-1B. Comparing the inner diameters of the channels 110, 120 shown in FIG. 1C to the inner diameters of the channels 210, 220 shown in FIG. 2C illustrates the increased channel inner diameter that can be achieved by forming an open edge along the length of at least one of the channels. Example sheath overall diameters may range from approximately 2.5 mm to approximately 4.5 mm, such as 3.7 mm or slightly smaller for use in a standard endoscopic device, and 3.2 mm or slightly smaller for use in a pediatric endoscopic device. Example individual channel inner diameters may range from approximately 0.5 mm to approximately 4 mm. However, it is appreciated that the sheath overall diameter and/or the channel inner diameters may be greater than or less than the illustrative examples provided herein, depending upon intended use and the dimensions of the endoscopic device used.

It is appreciated that, in other embodiments, both a first working channel and a second working channel may have an open edge formed along all or part of its length. It is further appreciated that, in other embodiments, the open edge of one or more of the channels may not be defined along the entire length of the channel, but may only be formed along a portion of the channel. For example, in one embodiment, a channel may include an open edge extending from its proximal end, which transitions to a completely enclosed channel that extends to the distal end from some intermediate point.

Another advantage of the open edge, such as the open edge 230 of a second channel 220 as shown in FIGS. 2A-2C, is that it permits greater range of movement of an instrument contained therein. For example, the sheath 200 may be inserted through a working channel of an endoscope, but may partially extend from the working channel in the proximal direction, as shown in and described with reference to FIG. 5A. Having an open edge 230 formed in the portion of the second channel 220 that extends from the endoscopic device allows the shaft of an instrument to be grasped and manipulated by the operator, and to be separated from the second channel 220, which in turn allows greater control over the instrument.

Yet another advantage of the open edge, such as the open edge 230 of a second channel 220 as shown in FIGS. 2A-2C, is that an instrument contained in the respective channel can be removed through the open edge instead of being pulled through one of the proximal or distal end of the sheath. This allows minimizing the diameter of the respective channel with an open edge, thus reducing the overall diameter of the sheath, while still accommodating instruments having a significant cross-sectional diameter. For example, as described in more detail herein, the second channel 220 may be adapted for housing a forceps instrument therein. Because of the open edge, the forceps instrument, for example the jaws, may have a cross-section diameter that is as large (or larger) than the inner diameter of the second channel 220. In this example configuration, the forceps instrument cannot be removed by pulling it through the channel due to the size of its jaws. However, the open edge allows the forceps instrument to be removed through the open edge of the channel (e.g., "pealing" out of the channel through the open edge), instead of pulling through the channel. It is appreciated that the open edge concept may be applied to other channels described herein, and is not to be limited to use with a forceps instrument.

In the embodiments shown in FIGS. 1A and 2A, the first channel 110, 210 has a length greater than the second channel 120, 220. In some embodiments, the overall length of the sheath may be anywhere between approximately 100 cm and approximately 300 cm. For example, a working channel of an endoscopic device may be between approximately 150 cm and approximately 200 cm in length, such as 180 cm, in one embodiment. Thus, the sheath 100, 200 may have a total length that is the same or similar as the working channel of the endoscopic device (e.g., between approximately 150 cm and approximately 200 cm, such as 180 cm), or may be longer, such as up to approximately 200 cm or more in length, to allow one or both of the first channel and the second channels to extend from the working channel's proximal and/or distal ends. Accordingly, in one embodiment, a sheath 100, 200 may have a length between approximately 100 cm or shorter (for use in shorter endoscopic devices) and approximately 300 cm or greater (for use in longer endoscopic devices). For example, in one embodiment, in which a sheath 100, 200 is configured to extend approximately 100 cm to approximately 110 cm from the working channel of an endoscopic device, then the sheath length may be approximately 250 cm to approximately 280 cm. It is appreciated, however, that, according to other embodiments, the overall sheath length may be greater than or less than the illustrative examples provided herein, depending upon intended use and the dimensions of the endoscopic device with which it will be used.

Moreover, in one embodiment, the first channel 110, 210 can be spaced apart from and extends beyond the second channel 120, 220 in both the proximal direction 102 and the distal direction 104. For example, according to one embodiment, the first channel 110, 210 extends distally beyond the second channel 120, 220 a distance between approximately 0.5 cm and approximately 10 cm, such as approximately 1 cm in one embodiment. Though, in other embodiments, the distance between the distal ends of the first channel 110, 210 and second channel 120, 220 can be greater than or less than that described herein, depending upon the intended use of the biopsy sheath.

Figure 5A:
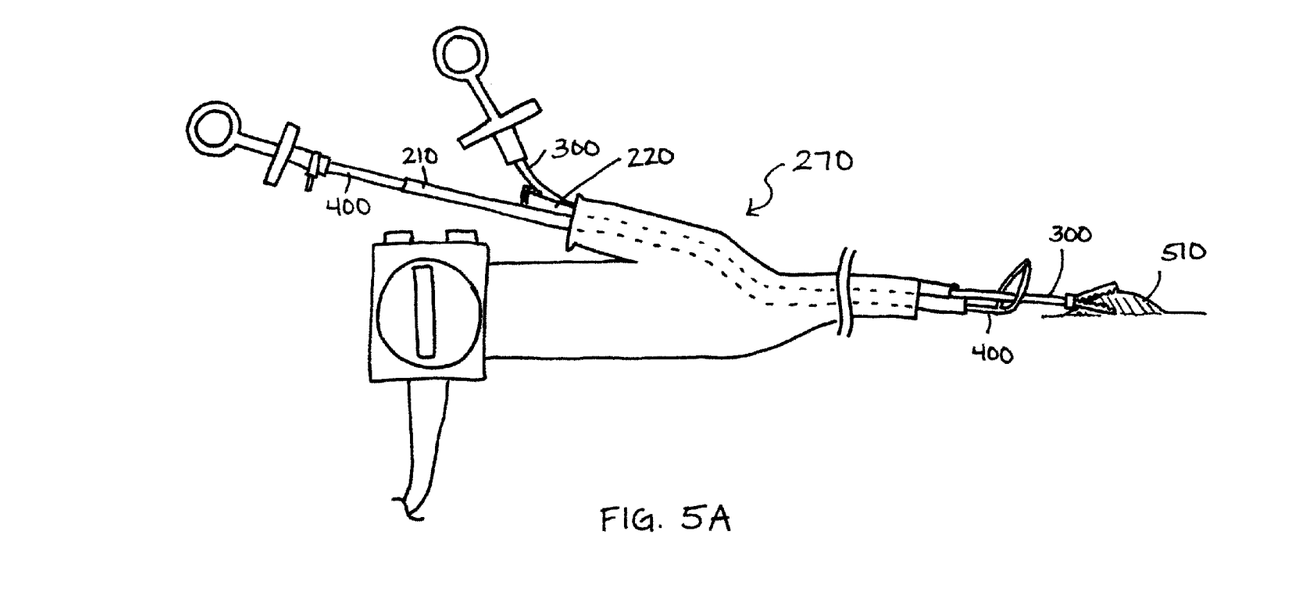
FIGS. 5A-5G are profile view schematic diagrams of a biopsy sheath in use with an endoscopic instrument, forceps instrument, and snare instrument, according to an example embodiment.
Figure 5B:
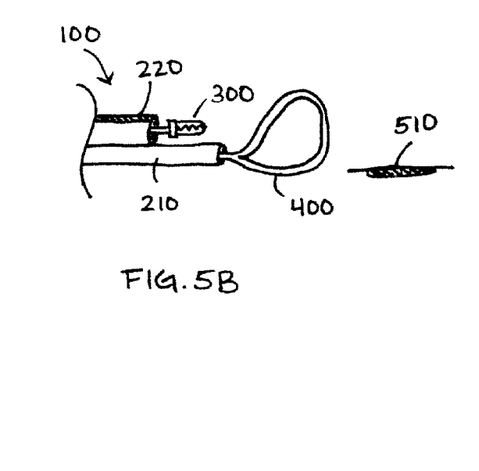
Figure 5C:
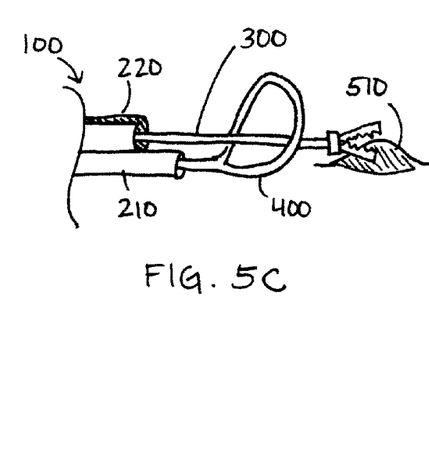
Figure 5D:
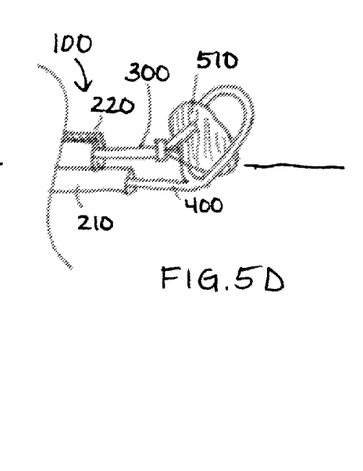

One benefit of a biopsy sheath having a distally extended first channel relative to the second channel is shown in FIGS. 5B-5D, illustrating various stages of using a snare instrument 400 placed through the first channel 210 and a forceps instrument 300 placed through the second channel 220 of a biopsy sheath 200. FIG. 5B shows an initial stage in which a snare instrument 520 in the first channel 210 that is pre-configured to naturally lie in the path of the second channel 220. Thus, the spaced apart and longer extending first channel 210 prevents interference of the snare instrument 400 with the end of the forceps instrument 300 when initially extending, or otherwise manipulating, the snare instrument 400 in the distal direction from the first channel 210. Otherwise, a snare instrument 400 pre-configured to lie in the path of the second channel 220 may undesirably interfere with a forceps (or other) instrument 400 extending from the second channel 220. Moreover, as shown in FIG. 5D, the spaced apart and longer extending first channel 210 provides a greater distance over which the forceps instrument 300 can extract in the proximal direction, pulling the polyp 510 through the loop of the snare instrument 400. Accordingly, one advantage of the spaced apart and distally extended first channel 210 relative to the second channel 220 is to allow unimpeded independent operation of instruments and ultimately greater control and range of movement of instruments when used in concert with each other, such as when the snare instrument 400 is preconfigured via shape memory techniques or any other means.

Also as shown in the embodiments illustrated in FIGS. 1A and 2A, the first channel 110, 210 is spaced apart from, and extends beyond, the second channel 120, 220 in the proximal direction 102. For example, according to one embodiment, the first channel 110, 210 extends proximally beyond the second channel 120, 220 a distance between approximately 50 cm and approximately 200 cm, such as approximately 110 cm in one embodiment. Though, in other embodiments, the distance between the proximal ends of the first channel 110, 210 and second channel 120, 220 can be greater than or less than that described herein, depending upon the intended use of the biopsy sheath.

FIG. 5A illustrates an advantage of both having a shorter second channel and an open edge in the second channel, according to one embodiment. In the embodiment shown in FIG. 5A, the biopsy sheath 200 includes a first channel 210 that extends proximally beyond a second channel 220 that has an open edge 230 formed along the length of the second channel 220. In this embodiment, a snare instrument 400 is placed within the first channel 210 and a forceps instrument 300 is placed within the second channel 220. As shown in FIG. 5A, the forceps instrument 300 (or any other instrument) can be manipulated along its length between its proximal end (e.g., at or near the operating mechanism) and its entry into the working channel of the endoscopic device 270 due to both the shorter second channel 220 relative to the first channel 210 and the open edge 230 of the second channel 220. Manual manipulation of the forceps instrument 300 closer to its distal end (e.g., at any point between its proximal end and the endoscopic device 270), while another operator (e.g., a technician, etc.) operates the operating mechanism (e.g., the handle), allows the operator better and more accurate control of the forceps instrument 210.

According to one embodiment, a biopsy sheath may be formed with multiple channels as a single device, such as via a poured mold or extrusion process. Though, in other embodiments, a biopsy sheath may be formed by subsequently bonding multiple separately-formed channels into a single device, such as heat fusion, chemical adhesion, mechanical means, or any other suitable techniques. According to various embodiments, a biopsy sheath may be formed from one or more biocompatible polymers, metals, metal alloys, or any combination thereof, which may be elastic, ridged, or any combination thereof.

Figure 3:
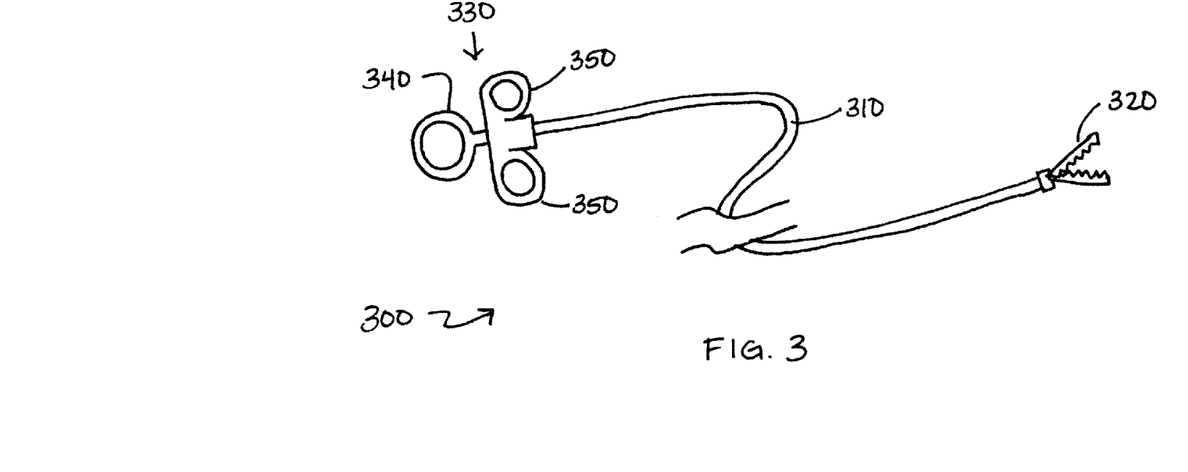
FIG. 3 is a profile view schematic diagram of a forceps instrument, according to an example embodiment.

FIG. 3 is a profile view schematic diagram of a forceps instrument, according to an example embodiment. The forceps instrument 300 can be any known elongated forceps instrument or other instrument adapted for use through a cannula and for grasping or otherwise capturing tissue. According to one embodiment, the forceps instrument 300 includes a shaft 310, which may be flexible, a grasping end 320, and an operating mechanism 330. The grasping end 320 is in operable communication with the operating mechanism 330 to allow an operator to selectively open and close (or any other manipulation, such as rotation, for example) the jaws of the grasping end 320. In one embodiment, as further described herein, one operator may manipulate the shaft 310 of the forceps instrument at or near the proximal end of a respective endoscope to maneuver the grasping end 320, while another operator (or the same operator) operates the operating mechanism 330 to actuate the grasping end.

The operating mechanism 330 can be configured in any suitable configuration to allow an operator to operably open and close the grasping end 320. For example, as is shown in FIG. 3, the operating mechanism 330 comprises a handle including at least one proximal ring 340 for receiving one or more digits and at least two distal rings 350 for receiving two opposed digits that are in slidable relation with the proximal ring 340. During operation, an operator places a thumb in the proximal ring 340 and the index and middle fingers in the two distal rings 350, allowing the operating mechanism 330 to be operated using a single hand by sliding the rings toward and away from each other, causing a reciprocating mechanism to actuate the grasping end 320 into open and closed positions. However, in other embodiments, the operating mechanism 330 may be configured in any number of configurations, including scissor-like handles, pistol grip handles with a squeezable member, or any other suitable mechanism for selectively actuating the grasping end 320.

Moreover, according to one embodiment, the operating mechanism 330 of the forceps instrument 300 may include a locking mechanism configured to provide selective locking of the handles in a desired position, such as locked in the open position, the closed position, or any position therebetween. A locking mechanism beneficially allows the grasping end 320 to remain engaged with a patient's tissue without requiring continued actuation of the operating mechanism 330, which may otherwise necessitate participation by a second operator/assistant. Any number of locking mechanisms can be included, such as, but not limited to, a releasable ratchet mechanism, a spring actuated pin and hole mechanism, a tension screw, a sliding wedge, and the like.

The grasping end 320 is shown in FIG. 3 as two opposed jaws having teeth or surfaces with increased friction. However, in other embodiments, the grasping end 320 may be configured in any number of configurations, including, but not limited to, a tripod grasping member, a spear member, a needle member, a net member, a cup member, or any other suitable mechanism for grasping or otherwise capturing tissue.

Accordingly, the forceps instrument 300 is insertable through one of the multiple channels of a biopsy sheath 100, 200, such as are described with reference to FIGS. 1A-2C, for grasping tissue, such as a polyp.

Figure 4:
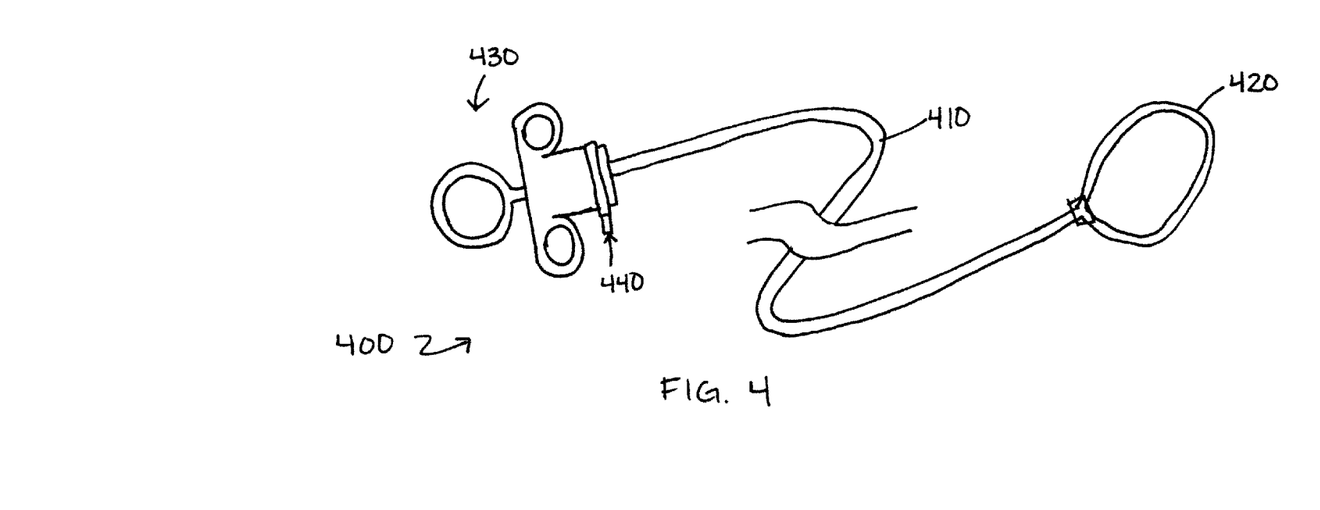
FIG. 4 is a profile view schematic diagram of a snare instrument, according to an example embodiment.

FIG. 4 is a profile view schematic diagram of a snare instrument, according to an example embodiment. The snare instrument 400 can be any known elongated snare instrument or other instrument adapted for use through a cannula and for encircling tissue, such as for removal. According to one embodiment, the snare instrument 400 includes a shaft 410, which may be flexible, a snare end 420, and an operating mechanism 430. The snare end 420 is in operable communication with the operating mechanism 430 to allow an operator to selectively actuate the snare end 420, such as to loosen or tighten the snare.

According to one embodiment, the snare end 420 is formed in a loop-like configuration that can be selectively opened (loosened) and closed (tightened). In one embodiment, the snare end 420 is configured to have one fixed end and one slidable end, whereby sliding the slidable end relative to the fixed end causes opening or closing the snare. However, any other suitable configurations for achieving selective opening and closing of a snare can be provided. The operating mechanism 430 of the snare instrument 400 for actuating the snare end 420 can be configured in any manner similar to those described above with reference to FIG. 3.

According to one embodiment, the snare end 420 has at least one preformed shape to extend at an angle from the axis of the shaft 410. For example, when the snare end 420 is within a channel (e.g., one of the channels 110, 120, 210, 220 of the sheaths 100, 200 in FIGS. 1A-2C), the snare end 420 is restrained by the inner walls of the channel, causing the snare end 420 to lie substantially along the same axis as the shaft. However, when extended past the distal end of a channel, the snare end 420 is unrestrained and thus resumes its preformed shape (e.g., extending angularly, etc.). In one embodiment, an angular orientation permits the snare end 420 to be positioned substantially around the axis of an adjacent channel, such as a channel retaining a forceps instrument. A forceps instrument can thus be extended and retracted through the snare without requiring additional manipulation of the snare end 420 by the operator. FIGS. 5B-5G illustrate the operation of a snare having a snare end with a preformed shape in cooperation with a forceps instrument 300, whereby the forceps instrument 300 is extended to grasp a polyp (or other tissue) (in FIGS. 5B-5C and 5E-5F) and subsequently retracted (in FIGS. 5D and 5G) through the snare end of the snare instrument 400.

Figure 5E:
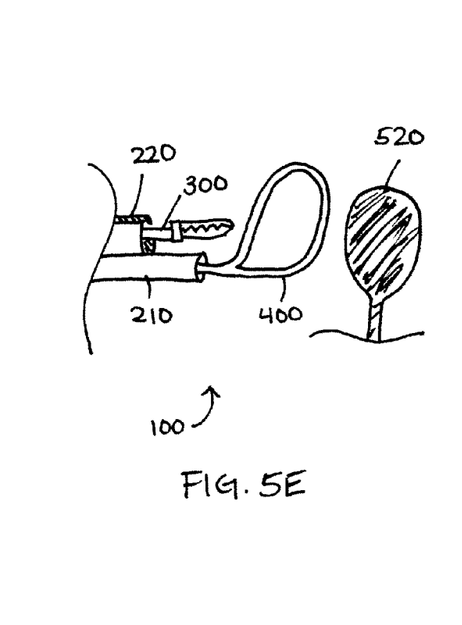
Figure 5F:
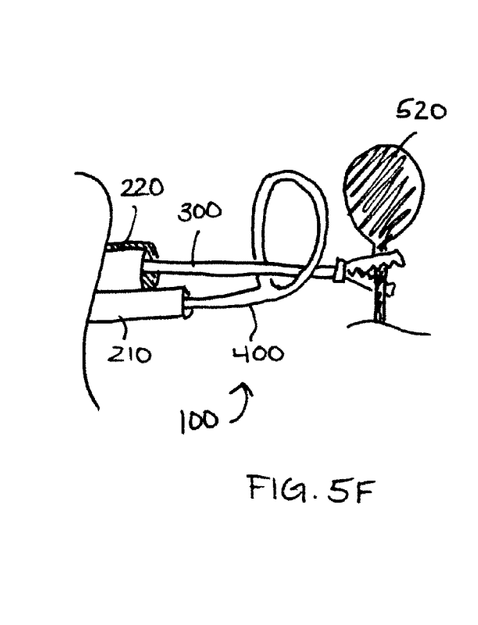
Figure 5G:
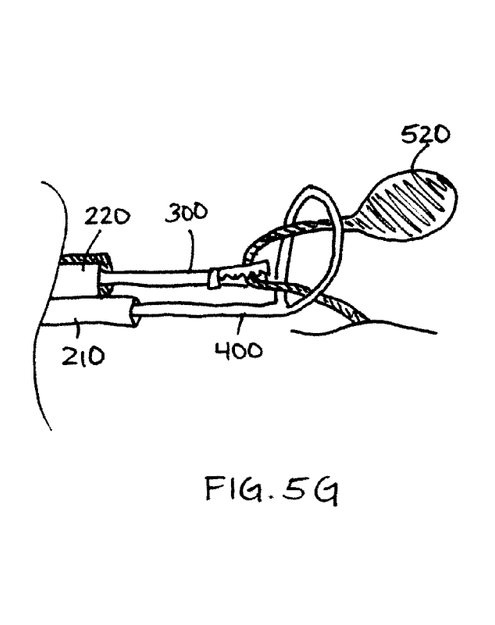

FIGS. 5R-5D illustrate an example biopsy procedure for removing a flat polyp 510 and FIGS. 5E-5G illustrate an example biopsy procedure for removing a pedunculated polyp 520. According to one embodiment, when removing a flat polyp, the forceps instrument 300 is extended to grasp the flat polyp to lift it and to give it additional shape, such as by pulling the tissue proximally, after which the snare instrument 400 can be extended to encircle and remove the polyp 510. For example, cautery may be applied to the snare instrument 400 after the forceps instrument 300 release the polyp and are retracted. In another example, however, cautery may not be applied to the snare instrument 400 to effect removal.

According to another embodiment, as shown in FIGS. 5E-5G, when removing a pedunculated polyp 520, the forceps instrument 300 can be extended to grasp the stalk of the polyp 520, allowing the snare instrument 400 to encircle the grasped portion of the stalk. Upon encircling the polyp stalk, the snare instrument 400 can sever the stalk, thus severing the polyp 520. Various techniques can be used to remove the severed polyp 520 (or polyp 510), which include grasping with the forceps instrument 300, suction, removal with another instrument (e.g., different forceps, spear, net, etc.), and the like.

According to another embodiment, the invention relates to devices and procedures for removing an ampulla at the distal aspect of the bile duct. In particular, the method comprises grasping a portion of the ampulla with a forceps instrument, encircling the portion of the ampulla with a snare instrument; and severing the ampulla with the snare instrument.

Any number techniques can be used to accomplish a snare end 420 having a preformed shape. Example techniques include, but are not limited to, a shape memory alloy (e.g., copper-zinc-aluminum-nickel alloy, copper-aluminum-nickel alloy, or nickel-titanium alloy, etc.) having a "memory" of at least one shape (and possibly more than one), mechanically formed and/or restrained, and the like. According to one embodiment, only the snare end 420 is manufactured with a preformed shape; however, in other embodiments, other portions of the snare instrument 400, such as the shaft 410, may have a preformed shape, such as may be useful when intended for use in specific procedures or at specific locations.

According to one embodiment, the snare instrument 400 may include a cauterizing mechanism, such as may be accomplished by the delivery of electrical energy to the snare end 420, to allow cauterizing tissue during removal via the heat caused by the electrical energy. A snare instrument 400 according to this embodiment may optionally be in electrical communication with an external power source and/or cauterization mechanism via a cautery input 440, to facilitate the delivery and control of electrical energy to the snare end 420. The forceps instrument 300 (or any other instrument used) may also optionally include a cauterizing mechanism, according to some embodiments. Accordingly, in one embodiment, the channel of the sheath through which a cauterizing instrument is to be inserted is enclosed along its length to provide electrical insulation, such as the first channel 110, 210 of the sheaths 100, 200 described with reference to FIGS. 1A-2C.

Accordingly, the snare instrument 400 is insertable through one of the multiple channels of a biopsy sheath 100, 200, such as are described with reference to FIGS. 1A-2C, for encircling and optionally removing tissue, such as a polyp.

According to various embodiments, the forceps instrument and/or the snare instrument may be formed from one or more biocompatible metals, metal alloys, polymers, and/or any combination thereof.

Figure 6:
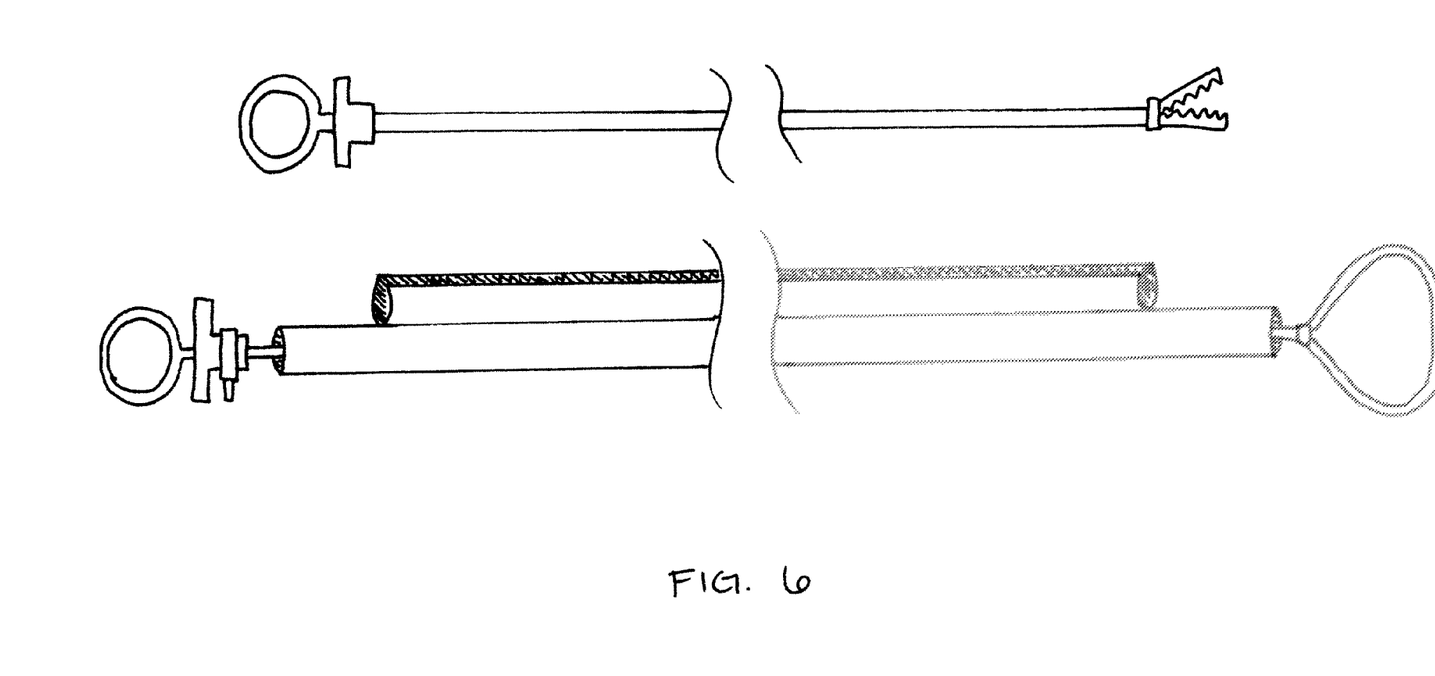
FIG. 6 is a profile view schematic diagram of a biopsy sheath shown with a forceps instrument and a snare instrument, according to an example embodiment.

FIG. 6 illustrates a profile view schematic diagram of a biopsy sheath shown with a forceps instrument and a snare instrument, according to an example embodiment. According to this embodiment, the biopsy sheath may be the same as or similar to the biopsy sheath 200 illustrated in and described with reference to FIGS. 2A-2C, having an open edge 230 formed along the length of the second channel 220. One benefit of an open edge 230 formed in at least one channel, in addition to reducing the overall diameter for improved fitment within a working channel of an endoscope, is to permit easy removal and/or manipulation of an instrument contained therein. As shown in FIG. 6, a snare instrument 400 is contained within a first channel 210 and a forceps instrument 300 can be contained within a second channel 220 having an open edge 230. The forceps instrument 300 is shown as removed from the second channel 220, illustrating the ease with which an instrument can be inserted and/or removed from the sheath 200 due to the open edge 230 of the channel. The forceps instrument 300 (or any other instrument) can be removed by extracting the forceps instrument 300 from the open edge 230 of the second channel 220, and can be inserted in the same manner. In one embodiment, the sheath 200 is configured such that an instrument contained within the channel is not easily extracted from an open end (e.g., if assembled within the channel, if having dimensions too great to be removed through the channel, etc.). Therefore, an open edge 230 provides the only easy means for removal and/or insertion of an instrument. Moreover, the open edge 230 permits reducing the diameter of the channel while still accommodating larger diameter instruments, such as those having approximately the same or similar diameter as the inner or outer diameter of the second channel 220. Thus, in embodiments in which larger diameter instruments are contained within the second channel 220, the open edge 230 allows for fast removal through the open edge 230.

Easy removal allows the removable instrument to be used separately from the sheath and the other instrument retained in the other channel, such as if the removable instrument is needed for use in a biopsy (e.g., cold biopsy, etc.) elsewhere during the procedure. Similarly, multiple different instruments may be used interchangeably within the open channel, allowing for increasing the number of types and/or sizes of instruments useable with the sheath 200. Moreover, as described above, a sheath 200 adapted for use with a forceps instrument 300 and a snare instrument 400, provides a multiple-use instrument capable of satisfying different surgical requirements, including a snare polypectomy using the snare instrument 400 when adapted for cauterization, a cold biopsy using the forceps instrument 300 (either within the sheath 200 or as part of a separate procedure when removed from the sheath 200), and/or a combination thereof. Accordingly, a sheath 200 with at least one channel with an open edge 230 increases the flexibility of removing an instrument for use elsewhere and/or interchanging instruments for use within the sheath 200, possibly reducing the number of individual instruments required to perform certain procedures. For example, during an operation when a snare polypectomy with cautery and a cold biopsy are to be performed, the sheath 200 with both the forceps instrument 300 and a cautery snare 400 can be used to perform the snare polypectomy with cautery, and the forceps instrument 300 can be removed from the sheath 200 to perform a separate cold biopsy, while only effectively using and incurring the cost of this multiple-use instrument. Moreover, it is appreciated that, according to other embodiments, a sheath may include more than one channel with an open edge, thus increasing the flexibility and use of the sheath and the number of instruments useable therewith, and possibly further reducing costs and the ability to share the instrument for use with multiple separate procedures for a patient.

Figure 7:
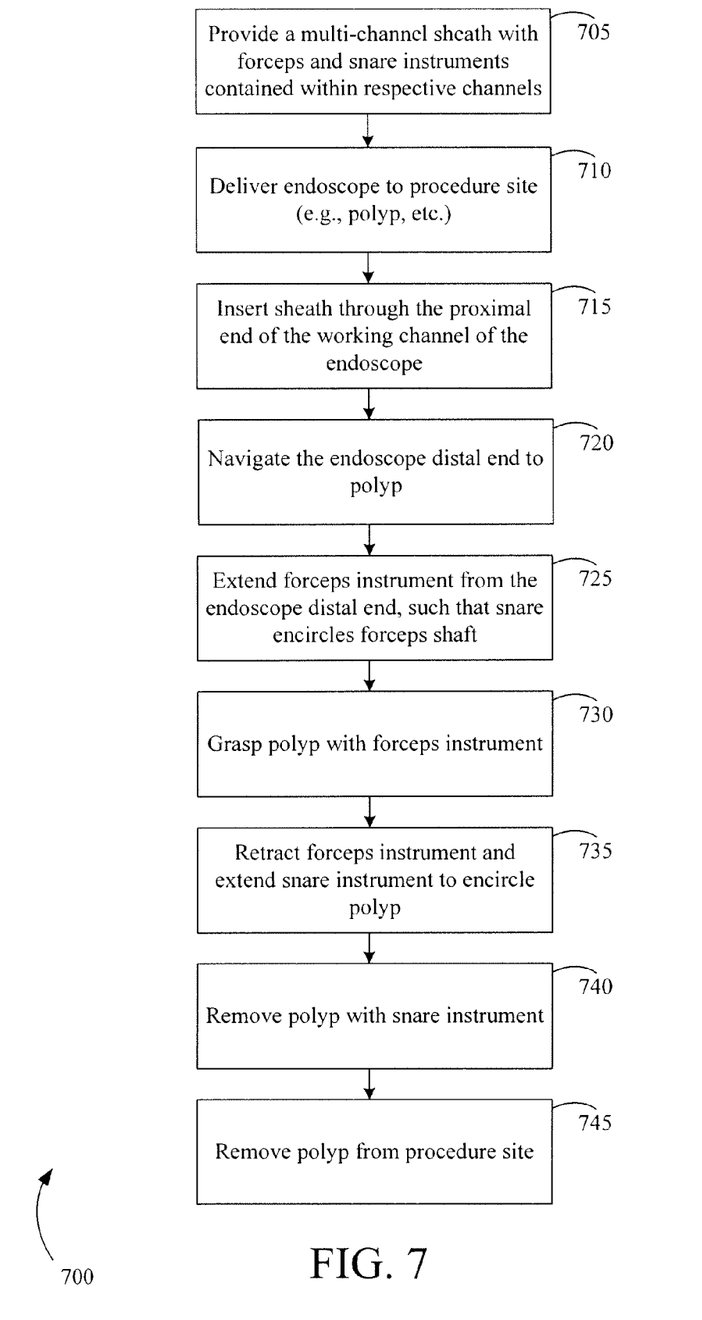
FIG. 7 is a method of performing an example endoscopic biopsy procedure, according to an example embodiment.

Accordingly, in use the sheath 200 can serve one or more functions when performing an endoscopic biopsy (or other) procedure for a patient. FIG. 7 illustrates an example method of performing an endoscopic biopsy procedure using a sheath, such as the sheath 200 described herein. The method 700 begins at block 705 in which a sheath having at least two channels, such as the sheath 200 described with reference to FIGS. 1A-2C, is provided. According to this embodiment, a forceps instrument and a snare instrument are provided within the respective channels of the sheath. At block 710, an endoscopic instrument (or endoscope) is delivered to the procedure site proximate a polyp to be removed. Any means known to localize a procedure site and to deliver an endoscope may be performed.

At block 715, the sheath housing the forceps instrument and the snare instrument are inserted through the proximal end of the working channel of the endoscope. The sheath may be inserted such that the proximal edge of the second channel (i.e., that with an open edge and containing the forceps instrument) is at or near the proximal end of the working channel. Doing so permits the shaft of the forceps instrument to extend proximally from the endoscope to allow easy manipulation by the operator and improved maneuverability of the grasping end of the forceps instrument.

At block 720, the distal end of the endoscope is navigated to the procedure site and proximate the polyp to be removed. In one embodiment, this may be performed after insertion of the sheath; though, in other embodiments, this may be performed during or prior to insertion of the sheath. At block 725, the forceps instrument is extended from the distal end of the endoscope and out of the working channel, such that the snare instrument encircles the shaft of the forceps instrument, which is shown by example in FIGS. 5B and 5E. Moreover, the separation between the distal end of the second channel (housing the forceps instrument) and the first channel (housing the snare instrument) increases the ease of manipulating and grasping the polyp by reducing interference between the two instruments and increasing the distance which the forceps instrument extends therefrom.

At block 730, the forceps instrument is used to grasp the polyp. If removing a flat polyp, then the forceps instrument can be used to grasp the polyp and to pull it distally to give it some shape and area to encompass and snare with the snare instrument, as shown in FIG. 5C. In one embodiment, saline (or other substance causing a similar effect) may be injected into the base of the polyp to cause it to lift and swell. If removing a pedunculated polyp having a stalk, then the forceps instrument is used to grasp the stalk of the polyp, as shown in FIG. 5F. At block 735, after grasping the polyp (or the stalk), the forceps instrument may be retracted proximally and/or the snare instrument may be extended distally such that the snare encircles the polyp (or a portion of the stalk), for removal at block 740. When removing a pedunculated polyp, the forceps instrument may be used to grasp and bend the stalk, such as to create a fold or otherwise manipulate the stalk shape to one that is more easily ensnared by the snare instrument, as shown in FIG. 5F. This may be accomplished by pulling the forceps instrument distally, or by creasing or folding by the forceps instrument. This procedure for removing a pedunculated polyp may be especially advantageous in situations in which a snare instrument cannot easily be placed over the polyp as conventionally done, but may be placed over a portion of the stalk grasped by the forceps instrument.

Finally, at block 745, the endoscope and severed polyp are removed from the patient. In one embodiment, the severed polyp may be removed with the entire endoscope, which may be accomplished at least in part by grasping with the forceps instrument, by suction applied through the endoscope, and/or by another instrument.

Accordingly, a new biopsy sheath is provided according to the various embodiments described and illustrated herein. These embodiments describe a multiple-channel sheath that allows at least two biopsy instruments to be used in concert through a single sheath. Moreover, the combination of a snare instrument and a forceps instrument is particularly advantageous for removal of flat polyps, as well as pedunculated polyps, but can be used for any polyp type or other tissue. The spaced apart orientation in combination with a preformed shape snare end allow better control and cooperation between a forceps instrument and a snare instrument when performing a biopsy procedure. In addition, with at least one channel having an open edge, the overall profile of the biopsy sheath can be minimized while increasing the inner diameter of the respective channels, which in turn increases the number and/or the size of instruments useable within the working channel of an endoscopic device due to the increased sheath inner diameters. Economic efficiencies are also gained in part because the biopsy sheath is a multiple-channel sheath that accommodates at least two instruments, reducing the overall costs of performing a biopsy, the costs billed to the patient, and increasing the flexibility of instruments useable therewith. Finally, the multiple channels allow the sheath to serve multiple purposes, such as for snare polypectomy, cold biopsy, and/or a combination thereof, with a single instrument. The open edge of at least one channel allows the instrument contained therein to be easily removed and used for other procedures for the patient, thus increasing simplicity and reducing costs. These and other advantages will be apparent based on the preceding description, the figures, and the following claims.

Modifications and variations of the methods and devices described herein will be obvious from the foregoing detailed description. Such modifications and variations are intended to come within the scope of the appended claims and the example inventions described herein.

What is claimed is:

1. A sheath for receiving a plurality of endoscopic instruments within separate channels thereof, comprising:
   a cross-sectional outer diameter and an inner diameter;
   terminally opposed proximal and distal ends, wherein the cross-sectional outer diameter of the distal end is adapted to be inserted into a working channel of an endoscopic device and wherein the cross-sectional outer diameter of the sheath defines an approximately hyperbolic shape that permits gas or fluid flow between an outer surface of the sheath and an inner surface of the working channel of the endoscopic device when the sheath is positioned therein;
   a length that is the distance between the proximal end and the distal end along a central axis between the proximal end and the distal end;
   a first channel and a second channel disposed longitudinally within the sheath, the each one of the first channel and the second channel having:
     a cross-sectional channel inner diameter;
     terminally opposed channel proximal and distal ends; and
     a length that is the distance between the channel proximal and distal ends along a central axis between the proximal and distal ends, and extending at least partially along the length of the sheath, wherein the second channel length is less than the first channel length, and wherein the distal end of the first channel extends distally beyond the distal end of the second channel,
   wherein at least one of the first channel or the second channel comprises an open edge open along at least part of the length of the respective channel, and
   wherein the sheath is adapted to be positioned within, and removable from, a working channel of an endoscopic device before, during and after deployment of the endoscopic device to a procedure site.

2. The sheath of claim 1, wherein the proximal end of the first channel extends proximally beyond the proximal end of the second channel.

3. The sheath of claim 1, wherein at least one of the first channel or the second channel has a length between approximately 100 cm and approximately 300 cm.

4. The sheath of claim 3, wherein the length of the first channel is greater than the length of the second channel by a length between approximately 50 cm and approximately 200 cm.

5. The sheath of claim 4, wherein the cross-sectional outer diameter of the sheath is between approximately 2.5 mm and approximately 4.5 mm.

6. The sheath of claim 5, wherein the cross-sectional inner diameter of the first channel is between approximately 0.5 cm and approximately 4 cm and the cross-sectional inner diameter of the second channel is between approximately 0.5 cm and approximately 4 cm.

7. The sheath of claim 2, wherein the second channel comprises an open edge open along its length, wherein a first instrument is contained within the first channel, and wherein a second instrument is insertable into and removable from the second channel through the open edge.

8. The sheath of claim 7, wherein the first channel is adapted to receive a snare instrument, and wherein the second channel is adapted to receive a forceps instrument.

9. A sheath for receiving a plurality of endoscopic instruments within separate channels thereof, comprising:
   terminally opposed proximal and distal ends, wherein the distal end is adapted to be inserted into a working channel of an endoscopic device;
   a length that is the distance along the central axis between the distal and proximal ends; and
   a first channel and a second channel disposed longitudinally within the sheath, each having opposed proximal and distal ends, the first channel and the second channel extending at least partially along the length of the sheath, wherein the length of the second channel is shorter than the length of the first channel and wherein at least one of the first channel or the second channel comprises an open edge open along at least part of the length of the respective channel.

10. The sheath of claim 9, wherein the proximal end of the first channel extends proximally beyond the proximal end of the second channel.

11. The sheath of claim 9, wherein the distal end of the first channel extends distally beyond the distal end of the second channel.

12. The sheath of claim 9, wherein the sheath has a cross-section that defines an approximately hyperbolic shape that permits gas or fluid flow between an outer surface of the sheath and an inner surface of a working channel of an endoscopic device when the sheath is positioned therein.

* * * * *